United States Patent [19]

McAleer et al.

[11] 4,242,324

[45] Dec. 30, 1980

[54] HEPATITIS B ANTIGEN

[75] Inventors: William J. McAleer, Ambler; Edward H. Wasmuth, Telford, both of Pa.

[73] Assignee: Merck & Co., Inc., Rahway, N.J.

[21] Appl. No.: 27,184

[22] Filed: Apr. 4, 1979

Related U.S. Application Data

[60] Continuation-in-part of Ser. No. 845,016, Oct. 25, 1977, Pat. No. 4,186,193, which is a division of Ser. No. 768,236, Feb. 14, 1977, abandoned, which is a division of Ser. No. 587,507, Jun. 16, 1975, Pat. No. 4,024,243.

[51] Int. Cl.³ ............................................. A61K 39/29
[52] U.S. Cl. .................................................... 424/89
[58] Field of Search ........................... 424/89; 435/238

[56] References Cited

U.S. PATENT DOCUMENTS

| | | | |
|---|---|---|---|
| 3,519,400 | 7/1970 | Anderson | 23/309 |
| 3,636,191 | 1/1972 | Blumberg et al. | 424/89 |
| 3,838,144 | 9/1974 | Leach | 260/112 R |
| 3,951,937 | 4/1976 | Vnek | 195/1.5 |
| 4,024,243 | 5/1977 | McAleer et al. | 424/89 |
| 4,031,203 | 6/1977 | Provost et al. | 424/89 |
| 4,088,748 | 5/1978 | McAleer et al. | 424/89 |
| 4,118,477 | 10/1978 | McAleer et al. | 424/89 |
| 4,129,646 | 12/1978 | McAleer et al. | 424/89 |
| 4,138,287 | 2/1979 | Andersson et al. | 195/1.5 |

OTHER PUBLICATIONS

Gerin et al., J. Virol., 4(5): 763-768, (1969), Biophysical Properties of Australia Antigen.
Bond et al., J. Inf. Dis., 125(3): 263, Mar. 1972, Separation and Purification of Hepatitis-Associated Antigen into Morphologic Types by Zonal Ultracentri Fugation.
Gerin et al., J. Virol, 7(5): 569-576, (1971), Australia Antigen: Large-Scale Purification from Human Serum and Biochemical Studies of Its Proteins.
Millman et al., J. Exp. Med., 131: 1190-1199, (1970), Australia Antigen A Hepatitis-Associated Antigen.

*Primary Examiner*—Shep K. Rose
*Attorney, Agent, or Firm*—Donald J. Perrella; Julian S. Levitt

[57] ABSTRACT

An improved process for the preparation of hepatitis B antigen by subjecting plasma of hepatitis B donors to isopycanic banding wherein the step gradient is NaBr. Faster and more economical processing is obtained by multiple loading of the step gradient, either NaBr or conventional gradients.

6 Claims, No Drawings

HEPATITIS B ANTIGEN

RELATED APPLICATIONS

This application is a continuation-in-part of application Ser. No. 845,016 filed Oct. 25, 1977, now U.S. Pat. No. 4,186,193, which is a division of application Ser. No. 768,236 filed Feb. 14, 1977, now abandoned, which, in turn, is a division of application Ser. No. 587,507 filed June 16, 1975, now U.S. Pat. No. 4,024,243.

BACKGROUND OF THE INVENTION

This invention relates to hepatitis B and, more particularly, to a vaccine for hepatitis B and to a method for purifying hepatitis B antigen for use as a vaccine.

Hepatitis B is one of the types of viral hepatitis which results in a systemic infection with the principal pathologic changes occuring in the liver. This disease affects mainly adults and is maintained chiefly by transfer of infection from long term carriers of the virus. Usual methods of spread are by blood transfusion, contaminated needles and syringes, through skin breached by cuts or scratches, by unsterilized dental instruments as well as by saliva, venereal contact or exposure to aerosolized infected blood.

The incubation period of type B hepatitis is relatively long: from 6 weeks to 6 months may elapse between infection and the onset of clinical symptoms. The illness usually begins with fatigue and anorexia, sometimes accompanied by myalgia and abdominal discomfort. Later jaundice, dark urine, light stools and tender hepatomegaly may appear. In some cases, the onset may be rapid, with appearance of jaundice early in association with fever, chills and leukocytosis. In other cases jaundice may never be recognized and the patient may be aware only of a "flu-like" illness. It is estimated that the majority of hepatitis infections result in a mild, anicteric illness.

It is, accordingly, an object of the present invention to provide an improved method for extracting hepatitis B surface antigen. Another object is to provide a faster and more economical method of extracting antigen. A further object is to provide antigen which is free of added cesium or potassium. These and other objects of the present invention will be apparent from the following description.

SUMMARY OF THE INVENTION

Plasma of hepatitis B donors is subjected to an isopycnic banding wherein the gradient is NaBr. Faster and more economical processing of the plasma is obtained by multiple loading of the step gradient whether the step gradient be NaBr or a conventional gradient.

DETAILED DESCRIPTION

The starting material for the purified hepatitis B surfacen antigen ($HB_sAg$) of the present invention is plasma obtained from hepatitis B donors, e.g., by plasmaphoresis. The level of antigen may be measured in known manner by radioimmune assay, passive hemagglutination or complement fixation. The plasma is cooled and the cryoprecipitate which forms is removed by light centriguation. The $HB_sAg$ in the resulting clarified plasma is isolated by an isopycnic banding step followed by a rate zonal banding step.

In isopycnic banding the partially purified concentrate is contacted with a liquid medium having a density gradient therein which includes the density of the specific antigen being isolated. The liquid medium is then subjected to ultracentrifugation to attain an equilibrium distribution of the serum components through the density gradient according to their individual densities. Successive fractions of the medium are displaced and those containing the desired antigen, i.e. the fractions having a density of from about 1.21 to about 1.24 g/cc, are separated. The application of this technique to the purification of $HB_sAg$ is described in German Specification No. 2,049,515 and U.S. Pat. No. 3,636,191. The concentrations of the solutions forming the gradient are selected so as to encompass the density range of from about 1.0 to about 1.41 g/cc. The liquid medium may be employed in the form of a linear gradient or a step gradient. Preferably it is employed in the form of a step gradient due to its inherent higher capacity for fractionation.

In rate zonal banding the partially purified concentrate is subjected to ultracentrifugation in contact with a liquid medium having a density gradient therein, but this time using the rate zonal technique, i.e., at a rate and for a period such that equilibrium is not attained, the $HB_sAg$ and other residual serum components being distributed through the medium according to their sedimentation coefficients in the medium. The concentrations of the solutions forming the step gradient are selected so as to encompass the density range of from about 1.0 to about 1.28 g/cc. The rate zonal step is carried out until the $HB_sAg$ resides in the 1.13 to 1.16 density region. At this point the $HB_sAg$ is separated from the bulk of the crude plasma proteins and, most significantly, is also separated from the macroglobulin complement of the plasma. If the rate zonal step is carried out such that the desired $HB_sAg$ antigen reaches its equilibrium position, i.e., about 1.18 to about 1.20 g/cc, it has been found that a plasma macroglobulin fraction will appear as a contaminant in the desired $HB_sAg$ antigen fraction.

The liquid media used in the isopycnic banding and rate zonal steps may be any density gradient in the appropriate ranges. Prior art solutes for such solutions include, e.g. sucrose, potassium bromide, cesium chloride, potassium tartrate and the like.

The isopycnic banding step is conveniently carried out in a centrifuge, for example, Electronucleonics-K, by filling the stationary rotor with saline solution, then successively displacing the saline solution upwards with aliquots of a liquid medium solution of increasing density until a step gradient is formed. The plasma is introduced at the top of the rotor displacing some of the highest density solution from the bottom. Typically, the volume of plasma is from about 15% to about 40% that of the step gradient. The centrifuge is brought up to speed through a programmed speed control system which prevents mixing during the initial reorientation phase. When equilibrium is attained and the product is in its power density position, the rotor is slowed down through the same system to prevent mixing upon reorientation to the original configuration. Then the gradient is drained from below and the proper density cut collected. A similar technique is used in the rate zonal bonding. The proper density cut from the rate zonal banding is the desired concentrate of hepatitis B antigen.

Due to the small size, approximately 20 nm, of $HB_sAg$ the isopycnic banding step is quite time consuming, requiring about 18 hours of centrifuging. As a result, even operating 24 hours a day, 7 days a week, it is possible to prepare only about 4 batches of clarified plasma per centrifuge. Productivity can be increased, of course, by utilizing additional centrifuges. This involves a tremendous capital investment, however, as each centrifuge costs about $100,000.

It has now been found that substantial increases in productivity and substantially reduced operating costs are obtained by multiple loading of the isopycnic banding gradient. Multiple loading means subjecting a sample of clarified plasma containing $HB_sAg$ to isopycnic banding conditions for a time sufficient to permit substantially all of the $HB_sAg$ in the clarified plasma to pass into the gradient but insufficient to achieve equilibrium, and repeating this step at least once with an additional sample of clarified plasma containing $HB_sAg$, before continuing the isopycnic banding conditions for a time sufficient to achieve equilibrium. If desired, a gradient may be loaded with up to about 6 samples of clarified plasma. As the time required for the $HB_sAg$ in the clarified plasma to enter the gradient is only a fraction of that required to reach equilibrium, and as the subsequent time required to reach equilibrium is the same whether the gradient is single or multiply loaded, substantial savings in time and reductions in unit processing costs are obtained.

While the increased productivity and reduced costs of the multiple banding technique of the present invention may be achieved with any suitable gradient, preferably the gradient is sodium bromide.

The isopycnic banding is carried out to equilibrium by centrifuging at from about $40,000 \times g$ to about $80,000 \times g$ for about 10 hours or beyond. It has been found, however, that by centrifuging the plasma for about 4 hours substantially all of the $HB_sAg$ is caused to move into the isopycnic banding gradient. Then the sample of spent plasma is removed and a fresh sample of plasma equal in volume to the first sample is layered onto the gradient. Centrifuging may then be continued as previously for about 10 hours or beyond to cause the $HB_sAg$ in both samples to move into the equilibrium density region of the gradient (1.21 to about 1.24 g/cc) to complete the banding. Alternatively the centrifuging may be continued for 4 hours, the spent plasma removed and a third sample of fresh plasma layered onto the gradient. This multiple loading procedure may be repeated six or even more times before completing the banding by centrifuging for about 18 hours.

The ratio of the charge (plasma) volume to the gradient volume is from about 1:3 to about 1:6. When a single plasma charge is applied to the gradient and centrifuged under isopycnic banding conditions (e.g. for from about 16 to about 20 hours at 30,000 rpms in the K-II centrifuge) the resulting product generally will have a protein content of approximately 4–10 mg/ml in a volume of 1.0 liter, depending on the amount of protein in the original plasma.

When a double charge of plasma is applied to the gradient and centrifuged under isopycnic banding conditions, (for from about 16 to about 20 hours at 30,000 rpms) the resulting product will have a protein content which is additive for the charges employed, typically from about 8–20 mg/ml in a volume of 1.0 liter, depending on the amount of protein in the original plasma. The level of protein increases in this manner for each subsequent charge of plasma applied to the gradient.

The product is then subjected to a rate zonal banding. The rate zonal banding is carried out until the $HB_sAg$ is in the density range of from about 1.13 to about 1.16 g/cc. Typically this takes for from about 16 hours to about 20 hours, preferably for from about 17 to about 18 hours, at from about $30,000 \times g$ to about $60,000 \times g$.

According to one aspect of the present invention the gradient is formed of sodium bromide whether or not the multiple loading technique is used. In contrast to heretofore used materials sodium bromide has definite advantages. The solubility of sodium bromide allows the use of high density solutions in the formation of gradients at refrigerator temperatures (2°–6° C.). There are definite economic advantages to using sodium bromide over a salt such as cesium chloride as well as not having to contend with the problem of human toxicity from residual and $HB_sAg$ bound cesium ions. In sodium bromide gradient any ions beyond to the $HB_sAg$, due to biophysical characteristics will be sodium ions which are very compatible with the human biological system and do not present toxocity problems.

The biophysical characteristics of the $HB_sAg$ particle as a negatively charged particle is well documented [J. Clinical Investigation 52, 1176 (1973); J. of Virology, 10, 469 (1972)]. In the presence of high concentrations of positively charged sodium ions there is formed a sodium-$HB_sAg$ particle by the attraction of opposite charges. This particle can be considered to be a complex or a salt. What ever it is called it is compatible with the human biological system. The $HB_sAg$ obtained by the preferred mode of carrying out the present invention is substantially free of other cations, particularly cesium and potassium ions.

The superior solubility of NaBr at lowered temperatures with respect to KBr permits the use of lowered temperatures more conducive to stability of biological materials. The use of a step gradient rather than a linear gradient is preferred as it accumulates impurities at the step boundaries and permits processing a larger volume of plasma in a single gradient.

The antigen of the present invention is useful per se as an antigen for hepatitis B and can be used as described in U.S. Pat. No. 3,636,191. The $HB_sAg$ antigen of the present invention is a highly purified product. The isopycnic banding step results in about a 100 fold purification $HB_sAg$ relative to normal plasma protein. The rate zonal step results in about a further 20 fold purification of $HB_sAg$ relative to normal plasma protein. The combination of the two steps result in about a 2000 fold purification of $HB_sAg$ relative to normal plasma protein. The resulting product has been shown to be substantially free of blood group substances A and B as measured by serological and electrophoresis techniques. In addition, the antigen of the present invention can be used as the starting material for the hepatitis B antigen of copending application Ser. No. 577,483, filed May 14, 1975.

The following examples illustrate the present invention without, however, limiting the same thereto.

EXAMPLE 1

The rotor of a centrifuge, Electronucleonics K, is filled with 8,400 ml of phosphate buffer. After running the rotor up to 10,000 rpm to degas the system, the following step gradient is pumped into the bottom of the stationary rotor:

1. 2,400 ml of 10% NaBr, $\rho=1.08$
2. 1,000 ml of 20% NaBr, $\rho=1.17$
3. 1,500 ml of 30% NaBr, $\rho=1.28$
4. 3,500 ml of 40% NaBr, $\rho=1.41$ Plasma containing Australia antigen (HB$_s$Ag), 1,750 ml, is pumped into the top of the stationary rotor displacing 1,750 ml of 40% NaBr from the bottom of the rotor. The rotor is accelerated to 30,000 rpm and run at this speed for 18 hours. After stopping the rotor 500 ml of HB$_s$Ag rich material in the 1.21–1.24 density region, is collected and dialyzed against phosphate buffer.

The rotor is then filled with phosphate buffer, degassed as above, and the following step gradient pumped into the bottom of the stationary rotor:
1. 2,400 ml of 5% sucrose, $\rho = 1.02$
2. 1,750 ml of 15% sucrose, $\rho = 1.06$
3. 1,750 ml of 25% sucrose, $\rho = 1.10$
4. 2,500 ml of 50% sucrose, $\rho = 1.23$ The HB$_s$Ag rich material from the NaBr isopycnic banding step, 500 ml, is pumped into the rotor top displacing 1,000 ml. of 50% sucrose out the rotor bottom. The rotor is then run at 28,000 rpm for 18 hours. After stopping the rotor, 500 ml of HB$_s$Ag rich material in the 1.135–1.165 density region is collected.

EXAMPLE 2

The rotor of a centrifuge, Electronucleonics K, is filled with 8,400 ml of phosphate buffer. After running the rotor up to 10,000 rpm to degas the system, the following step gradient is pumped into the bottom of the stationary rotor:
1. 2,400 ml of 10% NaBr, $\rho = 1.08$
2. 1,000 ml of 20% NaBr, $\rho = 1.17$
3. 1,500 ml of 30% NaBr, $\rho = 1.28$
4. 3,500 ml of 40% NaBr, $\rho = 1.41$ Plasma containing HB$_s$Ag, 1,750 ml, is pumped into the top of the stationary rotor displacing 1,750 ml of 40% NaBr from the bottom of the rotor. The rotor is accelerated to 30,000 rpm and run at this speed for 4 hours. The rotor is then stopped and 1,750 ml of 40% NaBr are pumped into the bottom of the rotor forcing the plasma out the top. An additional 1,750 ml of fresh plasma containing HB$_s$Ag are pumped into the top of the rotor displacing an equal volume of 40% NaBr out the bottom of the rotor. The rotor is then run at 30,000 rpm for 18 hours. After stopping the rotor 1,000 ml of HB$_s$Ag rich material in the 1.21–1.24 density region is collected and dialyzed against phosphate buffer.

The rotor is then filled with phosphate buffer, degassed as above, and the following step gradient pumped into the bottom of the stationary rotor:
1. 2,400 ml of 5% sucrose, $\rho = 1.02$
2. 1,750 ml of 15% sucrose, $\rho = 1.06$
3. 1,750 ml of 25% sucrose, $\rho = 1.10$
4. 2,500 ml of 50% sucrose, $\rho = 1.23$ The HB$_s$Ag rich material from the NaBr isopycnic banding step, 1,000 ml, is pumped into the rotor top displacing 1,000 ml. of 50% sucrose out the rotor bottom. The rotor is then run at 28,000 rpm for 18 hours. After stopping the rotor, 1,000 ml of HB$_s$Ag rich material in the 1.135–1.165 density region is collected.

EXAMPLE 3

The rotor of a centrifuge, Electronucleonics K, is filled with 8,400 ml of phosphate buffer. After running the rotor up to 10,000 rpm to degas the system, the following step gradient is pumped into the bottom of the stationary rotor:
1. 2,400 ml of 10% NaBr, $\rho = 1.08$
2. 1,000 ml of 20% NaBr, $\rho = 1.17$
3. 1,500 ml of 30% NaBr, $\rho = 1.28$
4. 3,500 ml of 40% NaBr, $\rho = 1.41$ Plasma containing HB$_s$Ag, 1,750 ml, is pumped into the top of the stationary rotor displacing 1,750 ml of 40% NaBr from the bottom of the rotor. The rotor is accelerated to 30,000 rpm and run at this speed for 4 hours. The rotor is then stopped and 1,750 ml of 40% NaBr are pumped into the bottom of the rotor forcing the plasma out the top. An additional 1,750 ml of fresh plasma containing HB$_s$Ag are pumped into the top of the rotor displacing an equal volume of 40% NaBr out the bottom of the rotor. The rotor is accelerated to 30,000 rpm and run at this speed for 4 hours. The rotor is then stopped and a third charge of 1,750 ml of fresh plasma containing HB$_s$Ag are pumped into the top of the rotor displacing an equal volume of 40% NaBr out the bottom of the rotor. The rotor is then run at 30,000 rpm for 18 hours. After stopping the rotor, 1,500 ml of HB$_s$Ag rich material in the 1.21–1.24 density region is collected and dialyzed against phosphate buffer.

The rotor is then filled with phosphate buffer, degassed as above, and the following step gradient pumped into the bottom of the stationary rotor:
1. 2,400 ml of 5% sucrose, $\rho = 1.02$
2. 1,750 ml of 15% sucrose, $\rho = 1.06$
3. 1,750 ml of 25% sucrose, $\rho = 1.10$
4. 2,500 ml of 50% sucrose, $\rho = 1.23$ The HB$_s$Ag rich material from the NaBr isopycnic banding step, 1,500 ml, is pumped into the rotor top displacing 1,500 ml of 50% sucrose out the rotor bottom. The rotor is then run at 28,000 rpm for 18 hours. After stopping the rotor 1,500 ml of HB$_s$Ag rich material in the 1.135 1.165 density region is collected.

EXAMPLE 4

The following table shows the marked increase in yield per unit of time when using the multiple loading technique of the present invention (Examples 2 and 3) as compared with single loading (Example 1).

| Example | Yield (ml) of HB$_s$Ag | Total isopycnic and rate zonal centrifuging time (hours) | % Increase in time (with respect to Example 1) | % Increase in yield (with respect to Example 1) |
| --- | --- | --- | --- | --- |
| 1 | 500 | 36 | — | — |
| 2 | 1,000 | 40 | 11.1% | 100% |
| 3 | 1,500 | 44 | 22.2% | 200% |

What is claimed is:

1. A complex formed by the association of positively charged sodium ions and negatively charged hepatitis B surface antigen, the complex being substantially free of other cations.

2. A complex according to claim 1 being substantially free of cesium ions.

3. A complex according to claim 1 being substantially free of potassium ions.

4. A complex according to claim 1 wherein the sodium ions are derived from sodium bromide.

5. A complex according to claim 1 wherein the hepatitis B surface antigen is derived from plasma.

6. A complex according to claim 5 wherein the sodium ions are derived from sodium bromide.

* * * * *